United States Patent
Lubart (12)

(10) Patent No.: US 6,379,939 B1
(45) Date of Patent: Apr. 30, 2002

(54) METHOD FOR INCREASING THE FERTILIZING CAPABILITY OF SPERM CELLS

(76) Inventor: Rachel Lubart, 10 Hankin Street, Tel Aviv 62506 (IL)

(*) Notice: Subject to any disclaimer, the term of this patent is extended or adjusted under 35 U.S.C. 154(b) by 0 days.

(21) Appl. No.: 09/670,081

(22) Filed: Sep. 26, 2000

(30) Foreign Application Priority Data

Jul. 18, 2000 (IL) ................................................ 137366

(51) Int. Cl.$^7$ .............................................. C12N 13/00
(52) U.S. Cl. ......................... 435/173.1; 435/2; 607/143
(58) Field of Search ......................... 435/2, 173.1, 375; 607/143

(56) References Cited

FOREIGN PATENT DOCUMENTS

EP          0872219 A1  * 10/1998

OTHER PUBLICATIONS

Product WS101 specifications [online] Zhoulin Bio–Spectrum Company, 1997 [retrieved Jun. 18, 2001] Retrieved from the Internet: <URL: http://168.160.224.165/english/product–ws101.htm>.*
Derwent Patent Abstract, "of SU 1724204, published Oct. 9, 1989, assigned to Grodno Med Inst (GRMI)".
Derwent Patent Abstract, "of SU 1267650, published Feb. 4, 1983, assigned to Lengd Doctors Advan (LEDO–R)".
Derwent Patent Abstract, "of RU 2035858, published Jul. 2, 1992, assigned to Akvatron Stock Co (AKVA–R)".
Derwent Patent Abstract, "of SU 1747083, published May 29, 1990, assigned to Mosco Pirogov Med Inst (MOPI)".
Cohen et al., "Light Irradation of Mouse Spermatozoa: Stimulation of In Vitro Fertilization and Calcium Signals", *Photochemistry and photobiology*, 1998, pp. 407–413, 68(3).
Soffer et al., Annual Meeting of the French Andrology Society, held at Issy–les–Moulinaux on Dec. 6–8, 1999.
T. Samuel et al., "Sperm–egg Penetration of Human Spermatozoa treated with Various Rabbit Antisera to Huamn Sperm Antigents", *Clin Exp Immunol*, 1987, pp. 454–459, 67.
H. Sato et al., "The Effects of Laser Light on Sperm Motility and Velocity in Vitro", *Andrologia*, 1984, pp. 23–25, 16(1).
R. Singer et al., "Low Energy Narrow Band Non–Coherent infrared Illumination of Human Semen and Isolated Sperm", *Andrologia*, 1991, pp. 181–184, 23.
A, Lenzi et al., "Laser Radiation and Motility Patterns of Human Sperm", *Archives of Andrology*, 1989, pp. 229–234, 23.

* cited by examiner

*Primary Examiner*—Remy Yucel
*Assistant Examiner*—Bronwen M. Loeb
(74) *Attorney, Agent, or Firm*—Browdy and Neimark, P.L.L.C.

(57) ABSTRACT

A method for improving the fertilizing capacity of sperm involves irradiating the sperm cells with light in the extended visible range (300–1,000 nm) having an intensity of 1 to 1,000 mW/cm$^2$ wherein the light substantially does not contain light outside the extended visible range and the light is not produced by laser.

15 Claims, No Drawings

METHOD FOR INCREASING THE FERTILIZING CAPABILITY OF SPERM CELLS

FIELD OF THE INVENTION

The invention relates to a method for improving the fertilizing capability of sperm cells.

BACKGROUND OF THE INVENTION

The effects of He—Ne laser irradiation on various aspects of cell metabolism have been recognized in recent years. Extensive literature exists on the application of low-power laser irradiation in various biological systems. The therapeutic effects of laser irradiation are usually attributed to the laser parameters, i.e. wavelength, intensity, coherency, polarization or monochromaticity of the light.

Cohen et al. *Photochemistry and Photobiology*, 1998, 68 (3), pp. 407–413 describes that irradiation of mouse spermatozoa with a 630 nm Helium Neon laser enhances their fertilizing potential. Breitbart et al. reported in the *Annual Meeting of the French Andrology Society*, held at Issy-les-Moulinaux on Dec. 6 to 8, 1999, that irradiation of human sperm with a low energy He—Ne laser improves the ability of poor quality sperm to penetrate egg cells.

SUMMARY OF THE INVENTION

The present invention is based on the surprising finding that the positive effect of He—Ne laser on sperm fertilizing capability, described by Cohen et al. and Breitbart et al, may also be achieved by any other light source having wavelengths ranging from about 300 to about 1000 nm. Light whose wavelength is in the above range will be referred to hereinafter as 'light in the extended visible range'. Light having wavelengths between 1000 and about 2000 nm is less efficient, and in any case is harmless to the cells. Therefore, a light source emitting light with a spectrum between, for instance, 600 to 2000 nm may also be used according to the invention.

Thus, the invention provides a method for improving the fertilizing capability of sperm cells by irradiating them with light in the extended visible range, having an intensity of 1 to 1000 $mW/cm^2$, provided that this light is not a He—Ne laser light. Preferably the light intensity is between 10 and 500 $mW/cm^2$, and more preferably between 40 and 100 $mW/cm^2$. The inventors found out that when only UVA light (i.e. light in the range from 300 to 400 nm) is used, an intensity of about 2 $mW/cm^2$ is preferable and when light in the range of 400 to 800 nm is used, 40 $mW/cm^2$ intensity is most preferable. The preferable intensity of light of the full extended visible spectral range may be roughly evaluated according to the spectrum of the light source, although the most preferable intensity is to be determined experimentally.

Preferably, the light irradiation should last for 0.5 to 10 minutes, more preferably between 2 and 5 minutes. In particular, the light irradiated on the sperm cells in accordance with the present invention may be any non-laser light, be it monochromatic or polychromatic, polarized or non-polarized, coherent or incoherent. Polychromatic in this sense may be any light having a spectrum broader than 5 nm, preferably broader than 20 nm. In particular, polychromatic light having a spectral breadth covering all the visible range, and possibly a wider range, such as the light emitted by a halogen lamp, may be implemented in the method of the invention. Another non-limiting example of a light source that may be used for the light irradiation in accordance with the invention is a light-emitting diode.

The method of the invention may also be carried out by irradiating the cells with any laser, which is not He—Ne, and which emits light in the extended visible range.

The method of the invention may be implemented by irradiating the sperm cells in vitro or in vivo. In the last case, if the sperm is of a mammal the epididymis of that mammal should be irradiated.

DETAILED DESCRIPTION

In order to understand the invention and to see how it may be carried out in practice, a non-limiting example is described hereinafter in detail.

The effect of light irradiation on human sperm penetration ability was studied using the Zona-free hamster egg (SPA) model. Ejaculated spermatozoa from 14 men were irradiated for 2 minutes with a halogen lamp, having a glass filter to filter out the light in the UVA range. The intensity of the illumination was 40 $mW/cm^2$. In controls, the illumination was omitted.

Ejaculates were allowed to liquefy for 10 to 30 minutes. A small aliquot (0.2 to 0.4 ml) was kept for analysis and the remaining volume was immediately diluted according to the semen viscosity in one or two volumes of Tes-Tris (TEST, Sigma Chemical Co, St Louis, Mo.) yolk buffer and kept in vertical tubes at 4° C. for 18 to 22 hours. At the end of incubation, the supernatant was carefully removed. Then, in addition to the protocol described by Samuel T, Soffer Y, and Caspi E in *Clin Exp Immunol* 1987; 67: pp. 454–9, a sperm layering and rise up procedure was done as follows: The sedimented sperm were resuspended in 0.25 ml Biggers, Whitten and Wittingham Buffer (BBW), enriched with 1.75% w/v bovine serum albumin (BSA), fraction V (Sigma Chemical Co), overlaid with 1 ml of the same medium in 30° inclined tubes and the sperm allowed to rise-up for one hour in a $CO_2$ incubator (at 37° C., under 5% $CO_2$ atmosphere and saturated humidity). The supernatant containing motile spermatozoa was centrifuged and sperm pellet resuspended in a small amount of BWW and finally adjusted to a concentration of 5 to $10 \times 10^3$ cells/ml. A 0.1 ml drop of this sperm suspension was prepared and kept in the $CO_2$ incubator until addition of eggs.

Female golden hamsters were superovulated as already described in the above-mentioned publication by Samuel et al. In this study, the females were 7 to 9 weeks old and operated on not later than 16 hours after human chorionic gonadotrophin (hCG) administration. The recovered eggs were kept at room temperature until insemination, and successively treated with Hyaluronidase (0.1 %, Sigma Chemical Co) and Trypsin (0.05%, Sigma Chemical Co) for the removal of cumulus and zona pellucida respectively. After thorough washing in 4 to 6 BWW drops, 20 to 30 zona-free eggs were immediately transferred for insemination to a sperm drop. The drops were covered with paraffin oil and further incubated for 3 hours. If the final sperm concentration was less than $5 \cdot 10^6$ cells/ml, the incubation was extended to 4 to 5 hours. Sperm preparations having less than $8 \cdot 10^5$ cells/ml were not used.

At the end of the incubation, the eggs were washed to remove unattached sperm, carefully flattened under a coverslip supported by four dots of paraffin-wax, and fixed with 2.5% gluteraldehyde (Sigma Chemical Co). Before staining with lacmoid stain (0.05%, Sigma Chemical Co), dehydration was performed, using a methylalcohol-acetic acid solution (40/60 v/v). The eggs were observed under a phase contrast microscope at a magnification of 400×. Penetration of eggs by sperm was indicated by the presence of swollen (decondensed) heads and/or tails in the egg cytoplasma. The percent of penetrated eggs and penetration index (total number of decondensed sperm/total number of eggs) were recorded.

The percentage of penetrated eggs (SPA percent) observed with irradiated sperm was compared to that of control. The results showed that 50% of the poor sperm increased SPA percent by 50% or more, while good sperm showed no improvement of SPA.

What is claimed is:

1. A method for improving the fertilizing capability of sperm cells comprising
    irradiating said sperm cells with light in the extended visible range, having an intensity of 1 to 1000 mW/cm2 and wherein said extended visible range is from about 300 to about 1000 nm,
    the light is not produced by laser,
        wherein said irradiated sperm cells have improved fertilizing capability.
2. A method according to claim 1 wherein said intensity is between 10 and 500 mW/cm$^2$.
3. A method according to claim 1 wherein said intensity is between 40 and 100 mW/cm$^2$.
4. A method according to claim 1 wherein said irradiation lasts for 0.5 to 10 minutes.
5. A method according to claim 1 wherein said irradiation lasts for 2 to 5 minutes.
6. A method according to claim 1 wherein said light is polarized.
7. A method according to claim 1 wherein said light is coherent.
8. A method according to claim 1 wherein said light is polychromatic light having a spectrum broader than 5 nm.
9. A method according to claim 1 wherein said light is emitted by a halogen lamp.
10. A method according to claim 1 wherein said light is emitted by a light emitting diode.
11. A method according to claim 1 wherein said light is non-polarized monochromatic light.
12. A method according to claim 1 wherein said sperm is contained in a body organ and said irradiation is carried out by irradiating said organ.
13. A method according to claim 8 wherein said polychromatic light has a spectrum broader than 20 nm.
14. A method according to claim 12 wherein said sperm is of a mammal and said organ is an epididymis.
15. A method according to claim 13, wherein said light has a spectral breadth of 400 nm or more.

* * * * *